United States Patent
Overstreet et al.

(10) Patent No.: US 7,076,308 B1
(45) Date of Patent: Jul. 11, 2006

(54) COCHLEAR IMPLANT AND SIMPLIFIED METHOD OF FITTING SAME

(75) Inventors: Edward H. Overstreet, Castaic, CA (US); Michael A. Faltys, Northridge, CA (US)

(73) Assignee: Advanced Bionics Corporation, Valencia, CA (US)

( * ) Notice: Subject to any disclaimer, the term of this patent is extended or adjusted under 35 U.S.C. 154(b) by 713 days.

(21) Appl. No.: 10/218,645

(22) Filed: Aug. 13, 2002

Related U.S. Application Data

(60) Provisional application No. 60/313,226, filed on Aug. 17, 2001.

(51) Int. Cl.
*A61N 1/36* (2006.01)

(52) U.S. Cl. ...................................................... 607/57

(58) Field of Classification Search ............ 607/55–57, 607/136, 137; 600/379
See application file for complete search history.

(56) References Cited

U.S. PATENT DOCUMENTS

| | | | |
|---|---|---|---|
| 3,751,605 A | 8/1973 | Michelson | |
| 4,400,590 A | 8/1983 | Michelson | |
| 4,495,384 A | 1/1985 | Scott et al. | |
| 4,819,647 A | 4/1989 | Byers et al. | |
| 5,603,726 A | 2/1997 | Schulman et al. | |
| 5,626,629 A * | 5/1997 | Faltys et al. | 607/57 |
| 5,938,691 A | 8/1999 | Schulman et al. | |
| 6,067,474 A | 5/2000 | Schulman et al. | |
| 6,078,838 A | 6/2000 | Rubinstein | |
| 6,129,753 A | 10/2000 | Kuzma | |
| 6,157,861 A | 12/2000 | Faltys et al. | |
| 6,195,585 B1 | 2/2001 | Karunasiri et al. | |
| 6,205,360 B1 | 3/2001 | Carter et al. | |
| 6,208,882 B1 | 3/2001 | Lenarz et al. | |
| 6,219,580 B1 | 4/2001 | Faltys et al. | |
| 6,249,704 B1 | 6/2001 | Maltan et al. | |
| 6,289,247 B1 | 9/2001 | Faltys et al. | |
| 6,295,467 B1 | 9/2001 | Kollmeier et al. | |
| 6,415,185 B1 | 7/2002 | Maltan | |

FOREIGN PATENT DOCUMENTS

WO    WO-03/015863 A2    2/2003

OTHER PUBLICATIONS

Rubinstein et al., "The Neurophysiological Effects of Simulated Auditory Prosthesis Simulation" Second Quarterly Progress Report NO1-DC-6-2111.

(Continued)

*Primary Examiner*—George R. Evanisko
(74) *Attorney, Agent, or Firm*—Bryant R. Gold; Philip H. Lee

(57) ABSTRACT

A bionic ear cochlear stimulation system has the capability to stimulate fast enough to induce stochastic neural firing, thereby acting to restore "spontaneous" neural activity. Such neurostimulation involves the use of a high rate pulsitile stimulation signal that is amplitude modulated with sound information. Advantageously, by using such neurostimulation, a fitting system may be utilized that does not normally require T-level threshold measurements. T-level threshold measurements are not required in most instances because the high-rate pulsitile stimulation, even though at levels that would normally be a sub-threshold electrical stimulus, is able to modulate neural firing patterns in a perceptible way.

4 Claims, 12 Drawing Sheets

OTHER PUBLICATIONS van Wieringen, et al., "Comparison of Procedures to Determine Electrical Stimulation Thresholds in Cochlear Implant Users", Ear and Hearing, vol. 22(6), (2001), pp. 528-538.

Faltys inventor for AB-257U; U.S. Appl. No. 10/218,616; filed Aug. 13, 2002; entitled "Bionic Ear Programming System".

Segel, Overstreet, Kruger, and Mishra inventors for AB-313U; U.S. Appl. No. 10/651,653, filed Aug. 29, 2003; entitled "System and Method for Fitting a Cochlear Implant Sound Processor Using Alternative Signals".

Overstreet inventor for AB-362U; U.S. Appl. No. 10/647,372; filed Aug. 25, 2003; entitled "Enhanced Methods for Determining Iso-Loudness Contours for Fitting Cochlear Implant Sound Processors".

Maltan, Miller, and Harrison inventors for AB-376U; U.S. Appl. No. 10/662,615; filed Sep. 30, 2003; entitled "Cochlear Implant Sound Processor with Permanently Integrated Replenishable Power Source".

Overstreet, Litvak, and Faltys inventors for AB-378U; U.S. Appl. No. 10/698,097; filed Oct. 31, 2003; entitled "Multi-Electrode Stimulation to Elicit Electrically-Evoked Compound Action Potential."

Overstreet inventor for AB-379U; U.S. Appl. No. 10/698,098; filed Oct. 31, 2003; entitled "Method and System for Generating a Cochlear Implant Program Using Multi-Electrode Stimulation to Elicit the Electrically-Evoked Compound Action Potential".

Zeng, et al., "Loudness of Simple and Complex Stimuli in Electric Hearing", Annals of Otology, Rhinology & Laryngology, vol. 104 (9) Part 2, Suppl. 166, Sep. 1995, pp. 235-238.

* cited by examiner

COCHLEAR IMPLANT AND SIMPLIFIED METHOD OF FITTING SAME

The present application claims the benefit of U.S. Provisional Patent Application Ser. No. 60/313,226, filed Aug. 17, 2001, which application is incorporated herein by reference.

BACKGROUND OF THE INVENTION

The present invention relates to cochlear implants, and more particularly to a cochlear implant and a simplified method for fitting such cochlear implant that, in many instances, does not require the use of measured minimum-perception thresholds.

Electrical stimulation of predetermined locations within the cochlea of the human ear through an intra-cochlear electrode array is described, e.g., in U.S. Pat. No. 4,400,590. The electrode array shown in the '590 patent comprises a plurality of exposed electrode pairs spaced along and imbedded in a resilient curved base for implantation in accordance with a method of surgical implantation, e.g., as described in U.S. Pat. No. 3,751,615. The system described in the '590 patent receives audio signals, i.e., sound waves, at a signal processor (or speech processor) located outside the body of a hearing impaired patient. The speech processor converts the received audio signals into modulated RF data signals that are transmitted by a cable connection through the patient's skin to an implanted multi-channel intracochlear electrode array. The modulated RF signals are demodulated into analog signals and are applied to selected ones of the plurality of exposed electrode pairs in the intra-cochlear electrode so as to electrically stimulate predetermined locations of the auditory nerve within the cochlea.

U.S. Pat. No. 5,938,691, incorporated herein by reference, shows an improved multi-channel cochlear stimulation system employing an implanted cochlear stimulator (ICS) and an externally wearable speech processor (SP). The speech processor employs a headpiece that is placed adjacent to the ear of the patient, which receives audio signals and transmits the audio signals back to the speech processor. The speech processor receives and processes the audio signals and generates data indicative of the audio signals for transcutaneous transmission to the implantable cochlear stimulator. The implantable cochlear stimulator receives the transmission from the speech processor and applies stimulation signals to a plurality of cochlea stimulating channels, each having a pair of electrodes in an electrode array associated therewith. Each of the cochlea stimulating channels uses a capacitor to couple the electrodes of the electrode array.

Other improved features of a cochlear implant system are taught, e.g., in U.S. Pat. Nos. 5,626,629; 6,067,474; 6,157,861; 6,219,580; 6,249,704; and 6,289,247, each of which patents is incorporated herein by reference.

The implantable cochlear stimulators described in the '629, '474, '861 and '580 patents are also able to selectively control the pulse width of stimulating pulses that are applied through the electrode array to the cochlea, and the frequency at which the stimulating pulses are applied.

The new generation of cochlear implants that have the enhanced processing power, and which can provide multiple platforms for delivering electrical stimuli to the auditory nerve, including high frequency pulsitile stimulation having current pulses of controlled amplitude, width and frequency, are frequently referred to as a "bionic ear" implant.

As the art of cochlear stimulation has advanced to produce bionic ear implants, the implanted portion of the cochlear stimulation system, and the externally wearable processor (or speech processor) have become increasingly complicated and sophisticated. It is also noted that much of the circuitry previously employed in the externally wearable processor has been moved to the implanted portion, thereby reducing the amount of information that must be transmitted from the external wearable processor to the implanted portion. The amount of control and discretion exercisable by an audiologist in selecting the modes and methods of operation of the cochlear stimulation system have increased dramatically and it is no longer possible to fully control and customize the operation of the cochlear stimulation system through the use of, for example, switches located on the speech processor. As a result, it has become necessary to utilize an implantable cochlear stimulator fitting system to establish the operating modes and methods of the cochlear stimulation system and then to download such programming into the speech processor. One such fitting system is described in the '629 patent. An improved fitting system is described in the '247 patent.

The '247 patent further highlights representative stimulation strategies that may be employed by a multichannel stimulation system. Such strategies represent the manner or technique in which the stimulation current is applied to the electrodes of an electrode array used with the stimulation system. Such stimulation strategies, all of which apply current pulses to selected electrodes, may be broadly classified as: (1) sequential or non-simultaneous (where only one electrode receives a current pulse at the same time); (2) simultaneous (where substantially all of the electrodes receive current stimuli at the same time, thereby approximating an analog signal); or (3) partially simultaneous pulsitile stimulation (where only a select grouping of the electrodes receive stimuli at the same time in accordance with a predefined pattern).

Typically, when the fitting systems described in the '629 or '247 patents are employed for multichannel stimulation systems, or when equivalent or similar fitting systems are employed, it is necessary to use directly measured threshold values and/or thresholds derived from the measurement of psycophysically-determined pseudo-comfort levels. That is, for each channel of the multichannel system, a minimum threshold level is measured, typically referred to as a "T" level, which represents the minium stimulation current which when applied to a given electrode associated with the channel produces a sensed perception of sound at least 50% of the time. In a similar manner, an "M" level is determined for each channel, which represents a stimulation current which when applied to the given electrode produces a sensed perception of sound that is moderately loud, or comfortably loud, but not so loud that the perceived sound is uncomfortable. These "T" and "M" levels are then used by the fitting software in order to properly map sensed sound to stimulation current levels that can be perceived by the patient as sound.

Disadvantageously, determining the "T" and/or "M" levels (or other required thresholds) associated with each channel of a multichannel stimulation system is an extremely painstaking and time-intensive task. Such determinations require significant time commitments on the part of the clinician, as well as the patient. Moreover, once determined one channel at a time, such levels may not be representative of actual threshold levels that are present during real speech. That is, preliminary data indicate that thresholds set in single channel psychophysics overestimate the actual threshold required when all channels are running during live speech. Such an overestimation appears to penalize patient performance, particularly performance in noise.

Hence, neural stimulation parameters which render threshold measurement unnecessary would dramatically reduce the time requirements for programming sequential and/or partially simultaneous pulsitile stimulation, as well as facilitate a higher probability of optimized programming for pediatric as well as adult populations where obtaining such measures are difficult.

As the ages of patients into which implantable cochlear stimulators are implanted decreases, it becomes increasingly more important to improve the fitting process and to minimize, or eliminate, the need to make threshold measurements. This is because very young patients, for example, two year olds, are unable to provide adequate subjective feedback to the audiologist for the audiologist to accurately "fit" the cochlear stimulation system optimally for the patient. Thus, what is needed is an improved apparatus and simplified method for fitting a speech processor where many of the threshold measurements previously required are no longer needed.

SUMMARY OF THE INVENTION

The present invention addresses the above and other needs by providing a cochlear implant that provides auto-conditioning with high resolution neurostimulation. Such neurostimulation involves the use of high rate pulsitile stimulation that is amplitude modulated with sound information. Advantageously, as a result of using such auto-conditioning with high resolution neurostimulation, a fitting system may be utilized that does not normally require T-level threshold measurements. T-level threshold measurements are not required in many instances because the high-rate pulsitile stimulation, even though at levels that would normally be a sub-threshold electrical stimulus during a single channel measurement, is able to modulate neural firing patterns in a perceptible way.

For purposes of the present application, "high rate" is defined as a stimulation rate greater than about 2 KHz (i.e., stimulation where the period, T, between successive biphasic stimulation pulses is less than about 500 microseconds ($\mu$S)). "Pulsitile" stimulation is considered to be any pulsed stimulation, e.g., biphasic stimulation, where the pulse width, PW, of each phase of the biphasic pulse is less than about 21 $\mu$S, e.g., 11 $\mu$S, although in some instances it may be longer, e.g., 32 $\mu$S or as long as 75 $\mu$S. These definitional terms are illustrated in the waveform diagram presented in FIG. 1, described below.

Advantageously, when such high rate pulsitile stimulation parameters are used, the cochlea implant user, in most instances, tends to have better speech performance without mapping low-level signals to single channel pyscophysical threshold levels. Thus, not only is it not necessary to measure, on a channel-by-channel basis, the pyscophysical threshold levels (T-levels) that have heretofore been required for purposes of cochlear implant fitting, thereby greatly reducing the time demands associated with the cochlear fitting process, but by avoiding such measurements, the user's performance improves.

In accordance with one aspect of the invention, there is provided a cochlear stimulation system that applies high rate pulsitile stimulation to the users's cochlea, thereby inducing perceptible low-level neuronal firing patterns.

In accordance with another aspect of the invention, a cochlear implant fitting process is provided wherein, in most instances, the channel-by-channel T-levels need not be measured.

In accordance with still another aspect of the invention, stochastic firing is restored to the auditory nerve, thereby enhancing thresholds, dynamic range and pyscophysical performance.

In accordance with yet a further aspect of the invention, individual neurons are stimulated by a cochlear implant at a rate faster than they are able to follow, thereby resulting in a randomization of interspike intervals. Advantageously, when the neuron is no longer phase-locked to the carrier pulse, the firing probability becomes a function of stimulus energy, and becomes much more like "natural" hearing.

BRIEF DESCRIPTION OF THE DRAWINGS

The above and other aspects, features and advantages of the present invention will be more apparent from the following more particular description thereof, presented in conjunction with the following drawings wherein.

Figure 1:
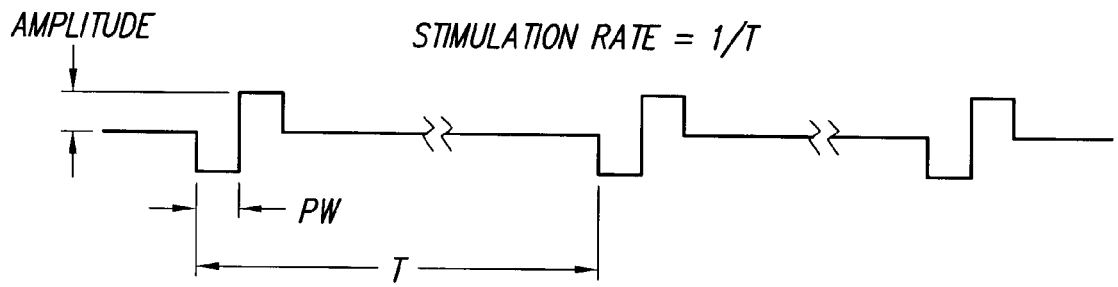
FIG. 1 is a current stimulation waveform that defines the stimulation rate (1/T) and biphasic pulse width (PW) associated with electrical stimuli, as those terms are used in the present application.

Appendix A provides an overview of one embodiment of a Fitting System that may be used with the invention.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

FIG. 1 shows a waveform diagram of a biphasic pulse train, and defines stimulation rate, pulse width and pulse amplitude as those terms are used in the present application.

Figure 2A:
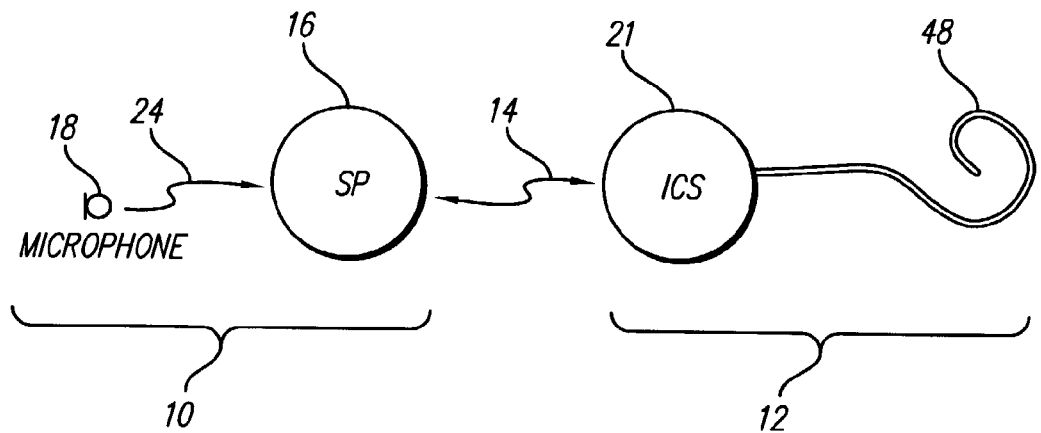
FIGS. 2A and 2B respectively show a cochlear implant system and a partial functional block diagram of the cochlear stimulation system, which system is capable of providing high rate pulsitile electrical stimuli in accordance with the invention.

FIG. 2A shows a bionic ear cochlear stimulation system that includes a speech processor portion 10 and a cochlear stimulation portion 12. The speech processor portion 10 includes a speech processor (SP) 16 and a microphone 18. The microphone 18 may be connected directly to the SP 16, or may be coupled to the SP 16 through an appropriate communication link 24. The cochlear stimulation portion 12 includes an implantable cochlear stimulator (ICS) 21, and an electrode array 48. The electrode array 48 is adapted to be inserted within the cochlea of a patient. The array 48 includes a multiplicity of electrodes, e.g., sixteen electrodes, spaced along its length that are selectively connected to the ICS 21. The electrode array 48 may be substantially as shown and described in U.S. Pat. No. 4,819,647 or 6,129,753, incorporated herein by reference. Electronic circuitry within the ICS 21 allows a specified stimulation current to be applied to selected pairs or groups of the individual electrodes included within the electrode array 48 in accordance with a specified stimulation pattern, defined by the SP 16.

The ICS 21 and the SP 16 are shown in FIG. 2A as being linked together electronically through a suitable data or communications link 14. In some cochlear implant systems, the SP 16 and microphone 18 comprise the external portion of the cochlear implant system; and the ICS 21 and electrode array 48 comprise the implantable portion of the system. Thus, the data link 14 is a transcutaneous data link that allows power and control signals to be sent from the SP16 to the ICS 21. In some embodiments, data and status signals may also be sent from the ICS 21 to the SP 16.

In a typical bionic ear implant system, as shown more particularly below in FIG. 2B, at least certain portions of the SP 16 are included within the implantable portion of the overall cochlear implant system, while other portions of the SP 16 remain in the external portion of the system. In general, at least the microphone 18 and associated analog front end (AFE) circuitry 22 will be part of the external portion of the system; and at least the ICS 21 and electrode array 48 are part of the implantable portion of the invention. As used herein, "external" means not implanted under the skin or residing within the inner ear. However, "external" may mean within the outer ear, including in the ear canal, and may also include within the middle ear.

Typically, where a transcutaneous data link must be established between the external portion and implantable portions of the system, such link is realized by an internal antenna coil within the implantable portion, and an external antenna coil within the external portion. In use, the external antenna coil is positioned so as to be aligned over the location where the internal antenna coil is implanted, allowing such coils to be inductively coupled to each other, thereby allowing data (e.g., the magnitude and polarity of a sensed acoustic signals) and power to be transmitted from the external portion to the implantable portion. Note, in other embodiments of the invention, both the SP 16 and the ICS 21 may be implanted within the patient, either in the same housing or in separate housings. If in the same housing, the link 14 may be realized with a direct wire connection within such housing. If in separate housings, as taught, e.g., in U.S. Pat. No. 6,067,474, incorporated herein by reference, the link 14 may be an inductive link using a coil or a wire loop coupled to the respective parts:

The microphone 18 senses acoustic signals and converts such sensed signals to corresponding electrical signals, and may thus be considered as an acoustic transducer. The electrical signals are sent to the SP 16 over a suitable electrical or other link 24. The SP 16 processes these converted acoustic signals in accordance with a selected speech processing strategy in order to generate appropriate control signals for controlling the ICS 21. Such control signals specify or define the polarity, magnitude, location (which electrode pair receives the stimulation current), and timing (when the stimulation current is applied to the electrode pair) of the stimulation current that is generated by the ICS. Such control signals thus combine to produce a desired spatiotemporal pattern of electrical stimuli in accordance with the desired speech processing strategy. Unlike early cochlear implant systems, the bionic ear implant system advantageously confines such control signals to circuitry within the implantable portion of the system, thereby avoiding the need to continually send or transmit such control signals across a transcutaneous link.

The speech processing strategy is used, inter alia, to condition the magnitude and polarity of the stimulation current applied to the implanted electrodes of the electrode array 48. Such speech processing strategy involves defining a pattern of stimulation waveforms that are to be applied to the electrodes as controlled electrical currents. In accordance with the present invention, an auto-conditioning with high resolution (ACHR) strategy is used which stimulates the implanted electrodes with a high rate pulsitile pattern that is amplitude modulated by the sound information. If multiple electrode pairs exist, as is the case with a multichannel cochlear implant system, then the types of stimulation patterns applied to the multiple channels may be conveniently categorized as: (1) simultaneous stimulation patterns, or (2) non-simultaneous stimulation patterns. Simultaneous stimulation patterns may be "fully" simultaneous or partially simultaneous. A fully simultaneous stimulation pattern is one wherein stimulation currents, either analog or pulsitile, are applied to the electrodes of all of the available channels at the same time. A partially simultaneous stimulation pattern is one wherein stimulation currents, either analog or pulsitile, are applied to the electrodes of two or more channels, but not necessarily all of the channels, at the same time. Examples of each type are given in U.S. Pat. No. 6,289,247, previously incorporated herein by reference.

Analog waveforms used in analog stimulation patterns are typically reconstructed by the generation of continuous short monophasic pulses (samples). The sampling rate is selected to be fast enough to allow for proper reconstruction of the temporal details of the signal. An example of such a sampled analog stimulation pattern is a simultaneous analog sampler (SAS) strategy.

Current pulses applied in pulsitile stimulation patterns are generally biphasic pulses, as shown in FIG. 1, but may also be multiphasic pulses, applied to the electrodes of each channel. The biphasic/multiphasic pulse has a magnitude (e.g., amplitude and/or duration) that varies as a function of the sensed acoustic signal. (A "biphasic" pulse is generally considered as two pulses: a first pulse of one polarity having a specified magnitude, followed immediately, or after a very short delay, by a second pulse of the opposite polarity having the same total charge, which charge is the product of stimulus current times duration of each pulse or phase.) For multichannel cochlear stimulators of the type used with the present invention, it is common to apply a high rate biphasic stimulation pulse train to each of the pairs of electrodes of selected channels in accordance with a selected strategy, and modulate the pulse amplitude of the pulse train as a function of information contained within the sensed acoustic signal.

Figure 2B:
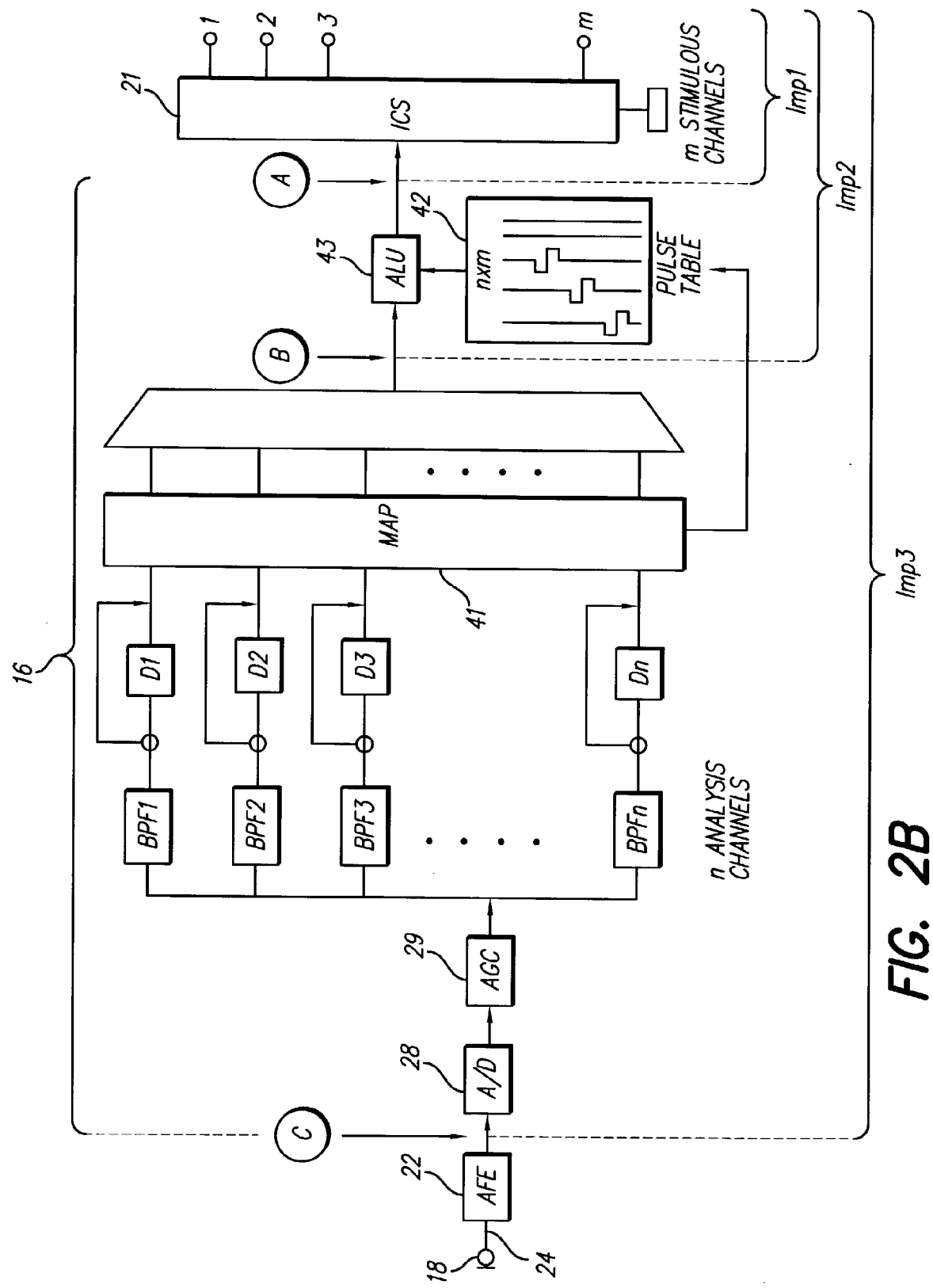

Turning next to FIG. 2B, a partial block diagram of a representative bionic ear cochlear implant is shown. More particularly, FIG. 2B shows a partial functional block diagram of the SP 16 and the ICS 21 of an exemplary bionic ear cochlear implant system capable of providing a high rate pulsitile stimulation pattern in accordance with the teachings of the present invention. That which is shown in FIG. 2B depicts the functions that are carried out by the SP 16 and the ICS 21. The actual electronic circuitry that is used to carry out these functions is not critical to understanding and practicing the present invention. It should also be pointed out that the particular functions shown in FIG. 2B are representative of just one type of signal processing strategy that may be employed (which divides the incoming signal into frequency bands, and independently processes each band). Other signal processing strategies could just as easily be used to process the incoming acoustical signal, and the present invention could still be used to provide added flexibility in specifying the stimulation patterns and waveforms that are selected and used with such additional signal processing strategies.

A complete description of the functional block diagram of the bionic ear implant shown in FIG. 2B is found in U.S. Pat. No. 6,219,580, previously incorporated herein by reference. It is to be emphasized that the bionic ear functionality shown in FIG. 2B is only representative of one type of exemplary bionic ear implant, and is not intended to be limiting. The details associated with a given bionic ear implant are not critical to understanding and practicing the present invention.

In the manner described in the U.S. Pat. No. 6,219,580, the bionic ear implant functionally shown in FIG. 2B provides n analysis channels that may be mapped to one or more stimulus channels. That is, as seen in FIG. 2B, after the incoming sound signal is received through the microphone 18 and the analog front end circuitry (AFE) 22, it is digitized in an analog to digital (A/D) converter 28, and then subjected to appropriate gain control (which may include compression) in an automatic gain control (AGC) unit 29. After appropriate gain control, the signal is divided into n analysis channels, each of which includes a bandpass filter, BPFn, centered at a selected frequency. The signal present in each analysis channel is processed as described more fully in the U.S. Pat. No. 6,219,580, and the signals from each analysis channel are then mapped, using mapping function 41, so that an appropriate stimulus current, of a desired amplitude and timing, may be applied through a selected stimulus channel to stimulate the auditory nerve.

Thus it is seen that the system of FIG. 2B provides a multiplicity of channels, n, wherein the incoming signal is analyzed. The information contained in these n "analysis channels" is then appropriately processed, compressed and mapped in order to control the actual stimulus patterns that are applied to the patient by the ICS 21 and its associated electrode array 48. The electrode array 48 includes a multiplicity of electrode contacts, connected through appropriate conductors, to respective current generators, or pulse generators, within the ICS. Through these multiplicity of electrode contacts, a multiplicity of stimulus channels, e.g., m stimulus channels, exist through which individual electrical stimuli may be applied at m different stimulation sites within the patient's cochlea.

While it is common to use a one-to-one mapping scheme between the analysis channels and the stimulus channels, wherein n=m, and the signal analyzed in the first analysis channel is mapped to produce a stimulation current at the first stimulation channel, and so on, it is not necessary to do so. Rather, in some instances, a different mapping scheme may prove beneficial to the patient. For example, assume that n is not equal to m (n, for example, could be at least 20 or as high as 32, while m may be no greater than sixteen, e.g., 8 to 16). The signal resulting from analysis in the first analysis channel may be mapped, using appropriate mapping circuitry 41 or equivalent, to the first stimulation channel via a first map link, resulting in a first stimulation site (or first area of neural excitation). Similarly, the signal resulting from analysis in the second analysis channel of the SP may be mapped to the second stimulation channel via a second map link, resulting in a second stimulation site. Also, the signal resulting from analysis in the second analysis channel may be jointly mapped to the first and second stimulation channels via a joint map link. This joint link results in a stimulation site that is somewhere in between the first and second stimulation sites. The "in between site" is sometimes referred to as a virtual stimulation site. Advantageously, this possibility of using different mapping schemes between n SP analysis channels and m ICS stimulation channels to thereby produce a large number of virtual and other stimulation sites provides a great deal of flexibility with respect to positioning the neural excitation areas in a location that proves most beneficial to the patient.

Still with reference to FIG. 2B, it should be noted that the speech processing circuitry 16 generally includes all of the circuitry from point (C) to point (A). In prior art cochlear implant systems, the entire SP circuitry was housed in a speech processor that was part of the external (or non-implanted) portion of the system. That is, in such prior art systems, only the ICS 21, and its associated electrode array, were implanted, as indicated by the bracket labeled "Imp1" (for "Implant-1"). This means that in such prior art systems, the signal passing through the serial data stream at point (A) is also the signal that must pass through the transcutaneous communication link from the external unit to the implanted unit. Because such signal contains all of the defining control data for the selected speech processing strategy, for all m stimulation channels, it therefore has a fairly high data rate associated therewith. As a result of such high data rate, either the system operation must be slowed down, which is generally not desirable, or the bandwidth of the link must be increased, which is also not desirable because the operating power increases.

In contrast to prior art systems, a modern bionic ear implant, such as the CII Bionic Ear system manufactured by Advanced Bionics Corporation of Sylmar, Calif., advantageously puts at least a portion of the speech processor 16 within the implanted portion of the system. For example, a bionic ear implant may place the Pulse Table 42 and arithmetic logic unit (ALU) 43 inside of the implanted portion, as indicated by the bracket labeled "Imp2" in FIG. 2B. Such partitioning of the speech processor 16 offers the advantage of reducing the data rate that must be passed from the external portion of the system to the implanted portion. That is, the data stream that must be passed to the implanted portion Imp2 comprises the signal stream at point (B). This signal is essentially the digitized equivalent of the modulation data associated with each of the n analysis channels, and (depending upon the number of analysis channels and the sampling rate associated with each) may be significantly lower than the data rate associated with the signal that passes through point (A). Hence, improved performance without sacrificing power consumption may be obtained with a bionic ear implant.

Future generations of bionic ear implant systems will incorporate more and more of the speech processor 16 within the implanted portion of the system. For example, a fully implanted speech processor 16 would incorporate all of the SP in the implanted portion, as indicated by the bracket labeled Imp3 in FIG. 2B. Such a fully implanted speech processor offers the advantage that the data input into the system, i.e., the data stream that passes through point (C), would need only have rate commensurate with the input acoustic signal.

The stimulation provided by a bionic ear implant in accordance with the present invention is premised on a stimulus pattern that induces stochastic, i.e., random, neural firing, which stochastic neural firing acts to restore "spontaneous" neural activity. Such stochastic neural firing results through application of a rapid stimulation pulse train applied by the speech processor circuits of the bionic ear cochlear implant. In operation, the high rate stimulus pattern provided by the invention stimulates individual neurons at a rate faster than the individual neurons can follow. This results in a randomization of inter-spike intervals, where the inter-spike interval is the time between successive neural firings for a given auditory neuron; or stated differently, inter-spike intervals represent the "firing patterns" of individual auditory nerve fibers. The inter-spike intervals, or firing patterns, of all auditory nerve fibers, even during the absence of sound, tend to be stochastic (random). Furthermore, these firing patterns are stochastic across the neural population. Advantageously, when the neuron is no longer phase-locked to the carrier pulse, its firing probability becomes a function of stimulus energy, and thus becomes more like "natural" hearing. Such randomization in a neural population better enables the population of neuron fibers to encode the fine details of sound. That is, the population of neuron fibers is able to encode what a single neuron fiber is not able to encode.

Figure 3B:
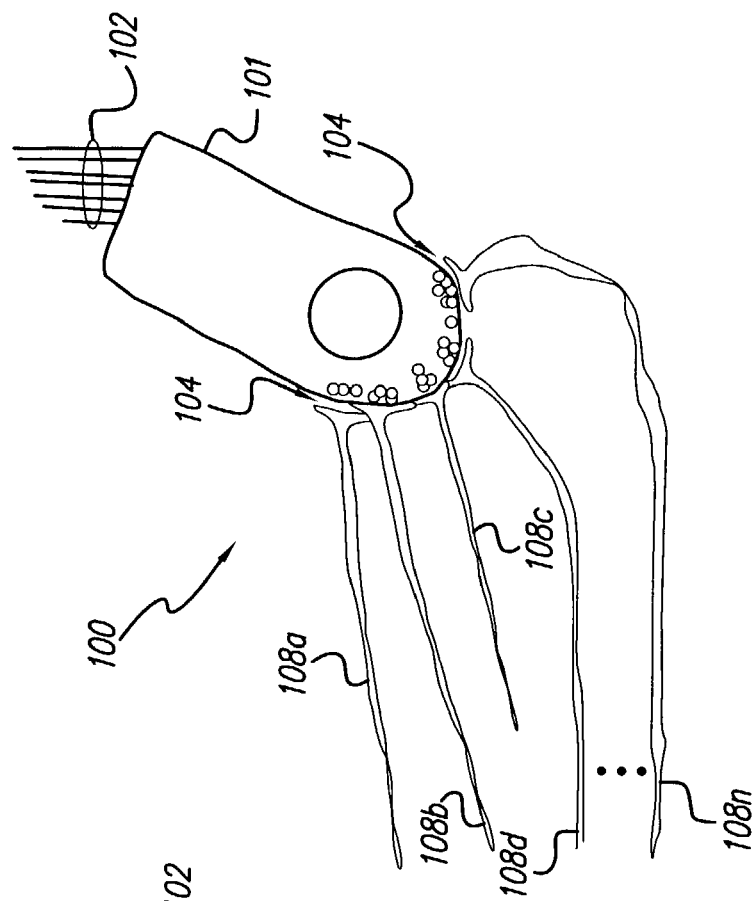
FIGS. 3A and 3B schematically illustrate the hair cells in the cochlea and the nerve fiber synapse which is the origin of stochastic spontaneous firing within the cochlea.
Figure 3A:
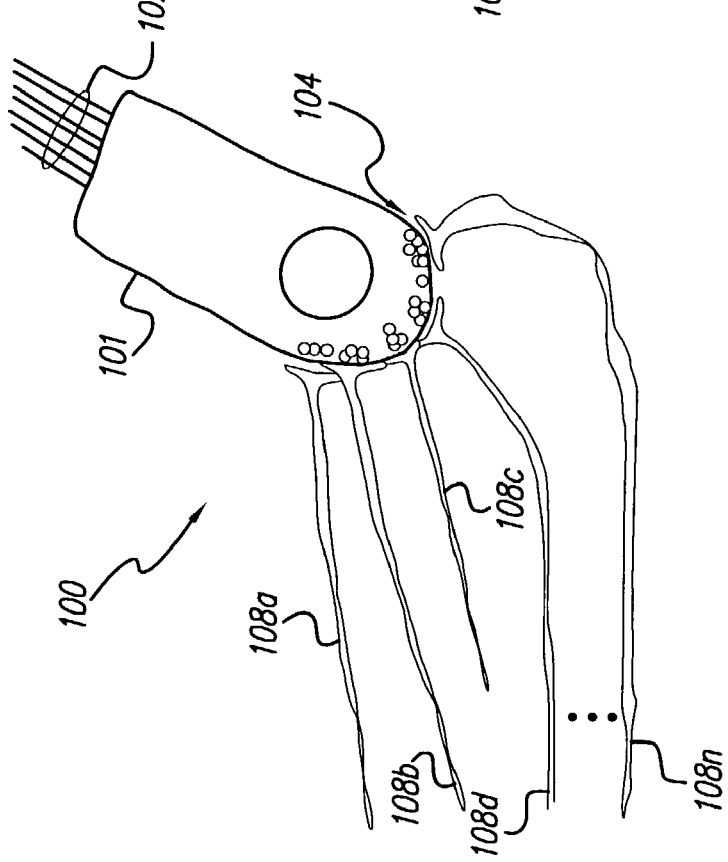

FIG. 3A schematically depicts an inner hair cell nerve fiber complex 100. Such nerve fiber complex includes an inner hair cell (IHC) 101, stereocilia hairs 102 at one end of the IHC 101, nerve fiber synapses 104 at the other end of the IHC 101, and auditory nerve fibers 108 connected to the synapses 104. The IHC 101 is the transduction cell, or sensory receptor, of the cochlea. At one end of the IHC 101 are tiny hairs 102, known as stereocilia, that are exposed on the inner surface of the cochlea. These hairs 102 move back and forth as the fluid in the cochlea moves back and forth, which movement causes a voltage to appear across an IHC membrane. (The fluid in the cochlea moves back and forth as a function of pressure waves, i.e., sound waves, sensed through the outer and middle ear or, in some instances, sensed through bone conduction.) At the other end of the IHC 101 are nerve fiber synapses 104. A synapse is a minute gap across which nerve impulses pass from one neuron to the next, at the end of a nerve fiber. Reaching a synapse, an impulse causes the release of a neurotransmitter, which diffuses across the gap and triggers an electrical impulse in the next neuron. In a healthy ear, the movement of the hairs or stereocilia 102 causes a nerve impulse to pass through the fiber complex 100 to the synapse 104. The nerve fiber synapse 104 is the origin of stochastic spontaneous firing. The nerve fiber synapses 104 are coupled to individual auditory nerve fibers 108*a*, 108*b*, 108*c*, 108*d*, . . . 108*n*, which nerve fibers (referred to collectively as the auditory nerve fiber 108), in turn, are coupled through ganglion cell bodies to the cochlear nerve, which forms part of the vestibulocochlear nerve (cranial nerve VIII) connecting with the brain.

It should be noted that it is technically not correct to refer to the IHC 101 as "firing" because, as indicated above, "firing" occurs at the nerve fiber synapse 104, not in the transductory IHC 101. The auditory nerve fiber 108 is the "spiking cell", where the effect of a nerve impulse passing through a synapse 104 is first manifest. As a short-hand way of referencing the chain of events that causes an auditory nerve fiber to become spiked, it is common to refer to the "firing of the auditory nerve", or the "firing of a ganglion cell" associated with the inner hair cell nerve fiber complex 100, or simply "neural firing".

When the stereocilia 102 are displaced, e.g., bent one way or the other as illustrated in FIG. 3B, the voltage across the IHC membrane changes. This causes the probability of transmitter release to also change (but the release is still random) as a function of stimulus energy.

At any instant of time, in response to sensed sound that causes the stereocilia 102 to be displaced, or in response to silence, where the stereocilia 102 remain substantially at rest, the nerve fiber synapses 104 fire in a stochastic (random) manner, causing nerve impulses to be sent along the respective auditory nerve fibers. As the stimulus energy increases, the probability that more nerve fibers will fire increases, but the firing remains stochastic, or random.

Figure 4A:
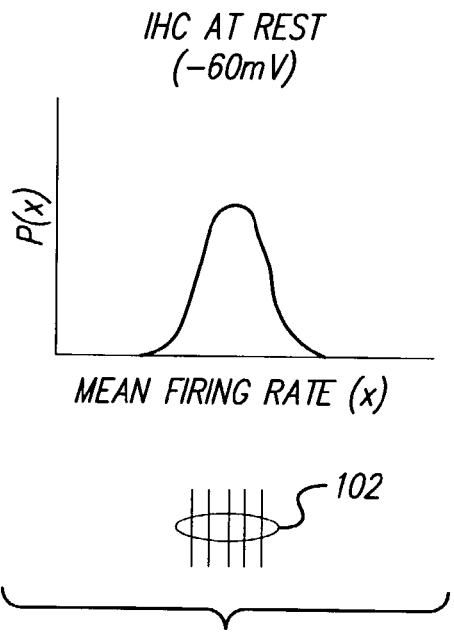
FIGS. 4A, 4B and 4C respectively illustrate the probability distribution of the average firing rate on an auditory nerve fiber as a function of differing inner hair cell (IHC) voltages.

FIG. 4A shows the average firing rate of an auditory nerve fiber as a function of the IHC voltage when the stereocilia 102 are not displaced and the IHC is at rest (and the IHC voltage is about −60 mV). As seen in FIG. 4A, such average firing rate has a probability distribution P(x) about a mean firing rate (x).

Figure 4B:
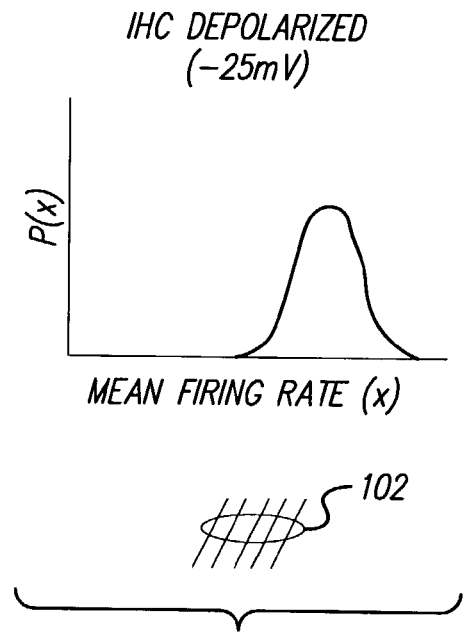

FIG. 4B shows the average firing rate of an auditory nerve fiber as a function of the IHC voltage when the IHC is depolarized, i.e., when the stereocilia 102 have been displaced in one direction, and the IHC voltage is about −25 mV. As seen in FIG. 4B, in such situation, the average firing rate (x) has a probability distribution P'(x) much like that shown in FIG. 4A, but the distribution has been shifted to the right, evidencing a faster mean firing rate.

Figure 4C:
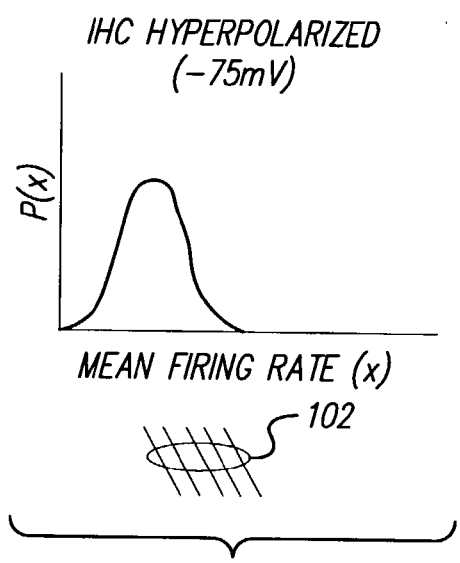

FIG. 4C shows the average firing rate of an auditory nerve fiber as a function of the IHC voltage when the IHC is hyperpolarized, i.e., when the stereocilia 102 have been displaced in the other direction, and the IHC voltage is about −75 mV. As seen in FIG. 4C, in such situation, the average firing rate (x) has a probability distribution P"(x) much like that shown in FIG. 4A, but the distribution has been shifted to the left, evidencing a slower mean firing rate.

Figure 5:
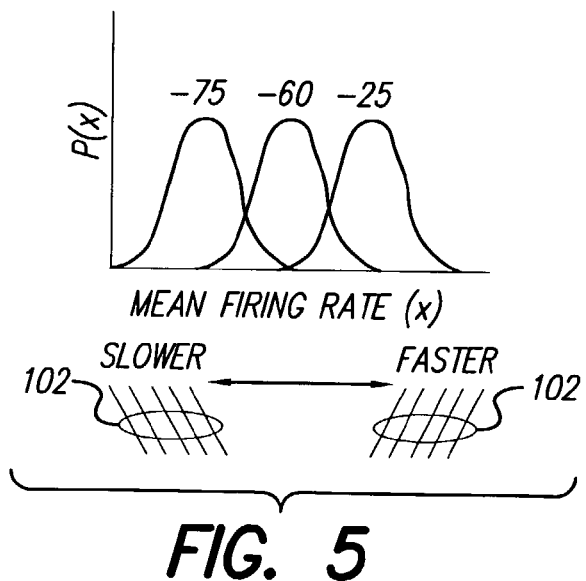
FIG. 5 shows, in one diagram, the average firing rate of an auditory nerve fiber as a function of IHC voltage.

FIG. 5 combines FIGS. 4A, 4B and 4C into one graph, and thus illustrates that as the IHC voltage changes from about −75 mV (for a hyperpolarized situation where the stereocilia 102 are displaced in one direction) to about −60 mV (for an at-rest situation where the stereocilia 102 are not displaced) to about −25 mV (for a polarized situation where the stereocilia 102 are displaced in the other direction) that the mean firing rate varies from a slow rate to a fast rate, but always in a stochastic manner, i.e., with a probability distribution associated therewith.

Figure 6:
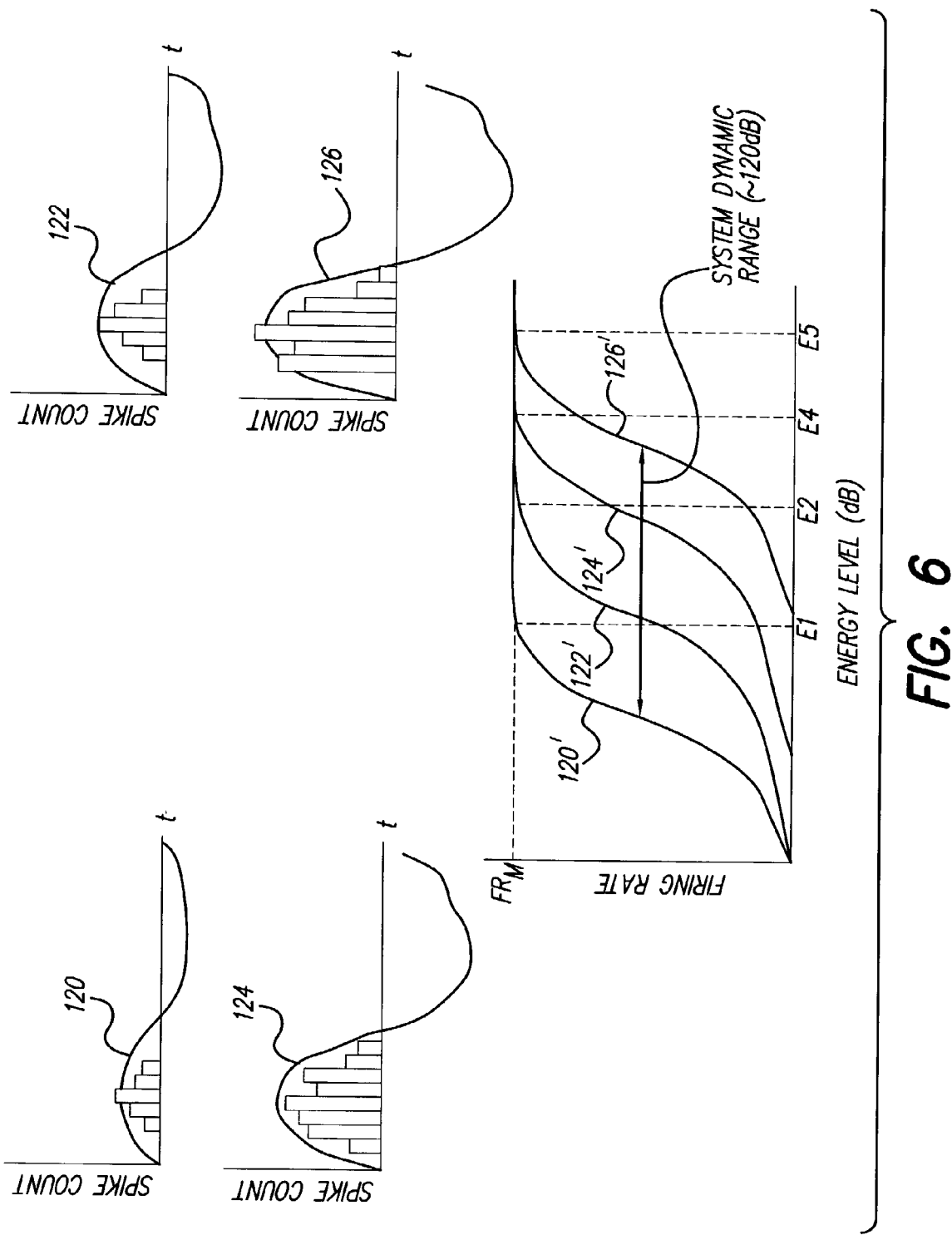
FIG. 6 illustrates how dynamic range is affected by the magnitude of a modulating signal.

Next, with reference to FIG. 6, a graph is shown that illustrates the system dynamic range achieved when the stochastic firing of the auditory nerve fibers remains intact. For low energy acoustic stimulation, as represented in graph 120, it is seen that the "spike count" (a histogram or "counting" of the number of firings that occur) follows a somewhat S-shaped curve 120' that starts at 0 and saturates, i.e., reaches a maximum firing rate $FR_M$, at energy level E1.

For a higher energy acoustic stimulation, as represented in graph 122, the spike count similarly follows a somewhat S-shaped curve 122' that starts near 0 and saturates at energy level E2. For still higher energy acoustic stimulation, as represented in graph 124, the spike count similarly follows an S-shaped curve 124' that starts near 0 and saturates at energy level E3. For even higher energy acoustic stimulation, as represented in graph 126, the spike count similarly follows a somewhat S-shaped curve 126' that starts near 0 and saturates at energy level E4. The system dynamic range is essentially the difference between the S-shaped curves 120' and 126', and is typically on the order of about 120 dB.

When the inner hair cells 101 are damaged or missing, as is usually the case for a patient experiencing sensorial hearing loss, then the auditory nerve fibers are silenced, and the patient has no hearing function. In order to awaken such auditory nerve fibers, and provide the patient with the sensation of hearing, it is known in the art to electrically stimulate the auditory nerve fibers using a cochlear implant.

Figure 7:
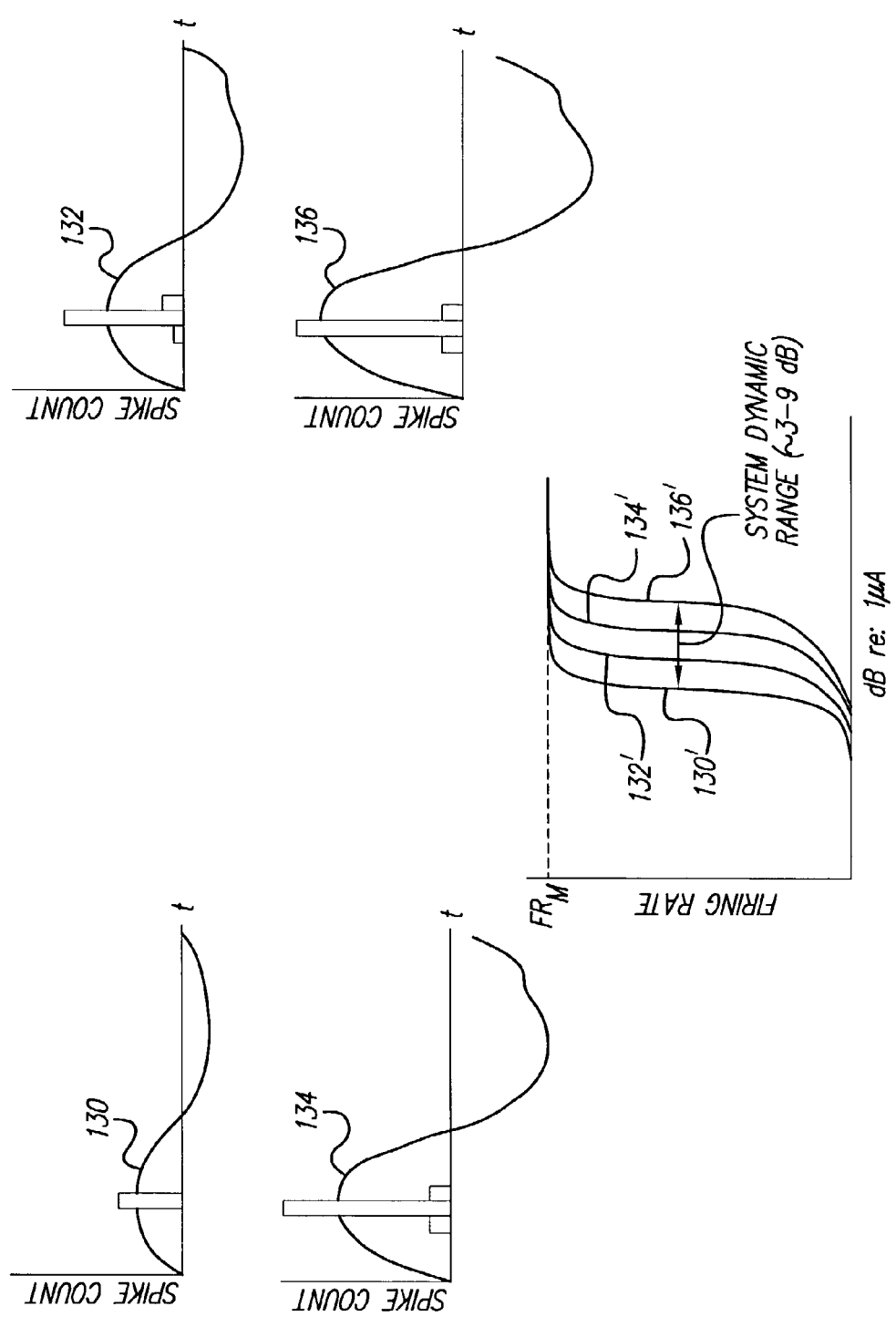
FIG. 7 shows how dynamic range is significantly narrowed when traditional electrical stimulation is employed.

Disadvantageously, the stimulation patterns employed by most cochlear implants result in a very narrow system dynamic range for the patient. This is because, as seen in FIG. 7, the electrical stimulation applied to the auditory nerve is always set to have an amplitude that is at least as great as the measured threshold T so that it will always cause the auditory nerve to fire. Moreover, it is always delivered at a precise time, usually being frequency locked with some type of clock signal that is phase locked, in one form or another, with the frequency of the sound signal that is to be perceived. Thus, as seen in FIG. 7, a low level stimulus, shown in graph 130, which by definition should still be above the minimum threshold T, causes the auditory nerve to fire at a controlled time, e.g., as determined by the system clock signal. The result is a firing-rate curve 130', typical of threshold-based systems, where firing begins to occur only when the threshold is exceeded, and at the rate of the applied stimulus (which, as indicated, is typically frequency-locked to a carrier signal) and the firing rate quickly saturates thereafter at the maximum firing rate, $FR_M$. (The $FR_M$ is typically the maximum rate that a given IHC complex 100 is able to follow.) A similar situation occurs as the energy of the applied stimulus increases, all of which energies are above the threshold T, as shown in graphs 132, 134 and 136, resulting in firing-rate curves 132', 134' and 136'. The resulting system dynamic range is very narrow, e.g., on the order of 3–9 dB.

Figure 8A:
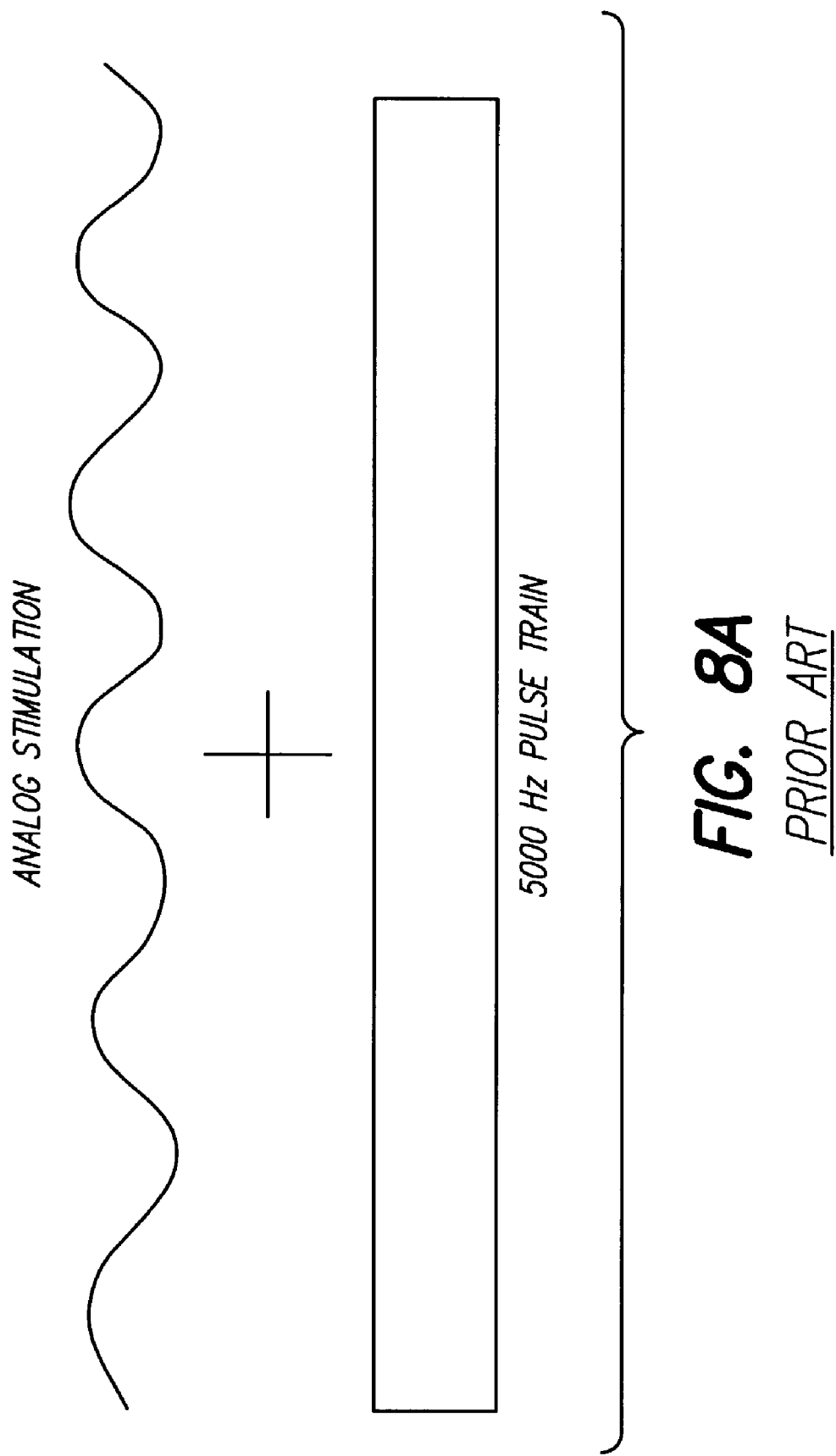
FIG. 8A illustrates one method known in the art for inducing stochastic neural firing using a cochlear implant.
Figure 8B:
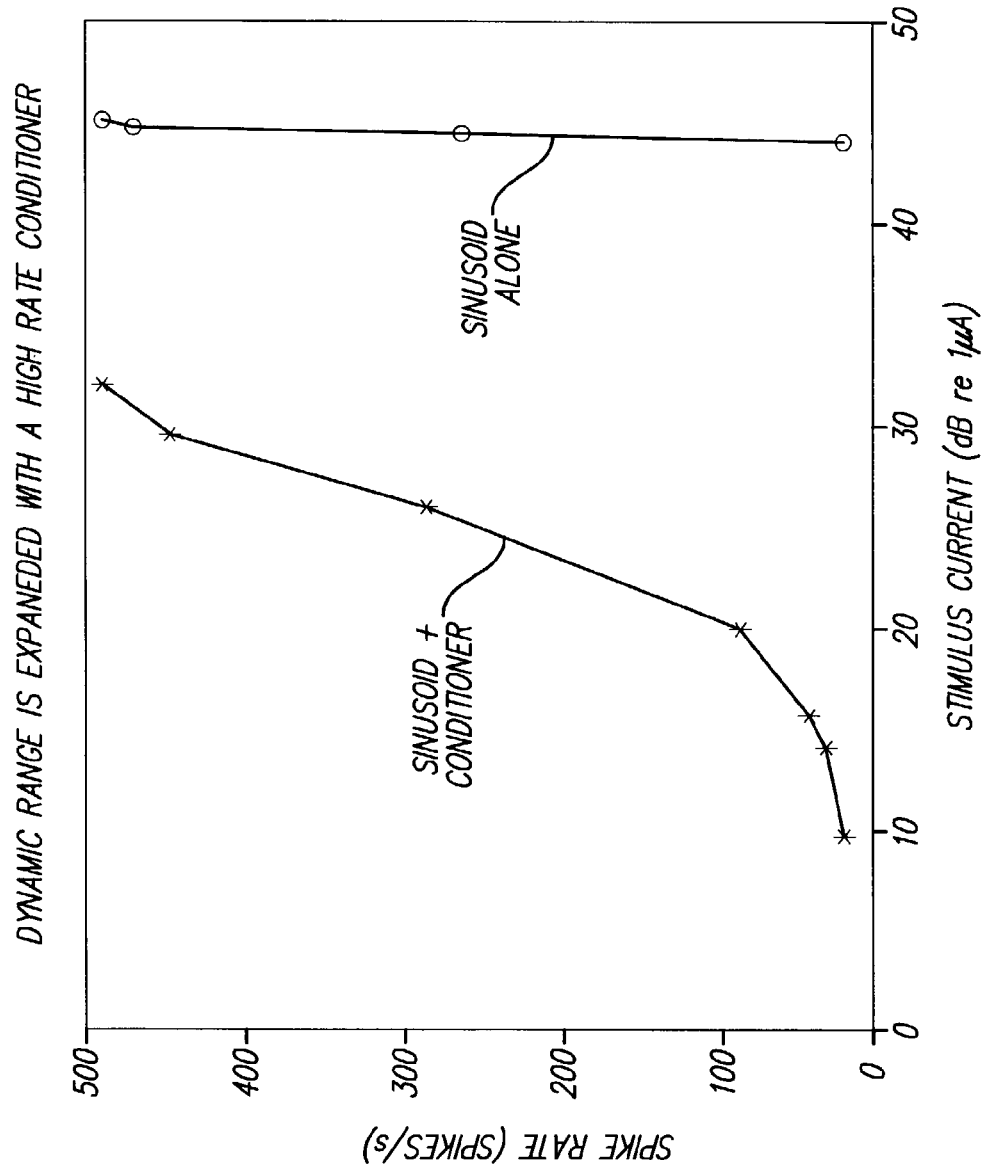
FIG. 8B shows how the method of FIG. 8A expands dynamic range.

One approach known in the art for expanding the dynamic range achieved with a cochlear implant is to apply a high rate conditioning signal, e.g., a 5000 Hz pulse train, in combination with analog stimulation to the electrode contacts. The 5000 Hz pulse train functions as a conditioner. See, Rubinstein et al., Second Quarterly Progress Report NO1-DC-6-2111. See also U.S. Pat. No. 6,078,838, incorporated herein by reference. This approach, and the results achieved thereby, are illustrated in FIGS. 8A and 8B. Disadvantageously, the approach proposed by Rubinstein et al. requires a painstaking process to determine the level of the non-information conditioner pulse train. Moreover, because it is combined with analog stimulation, the power consumption is exorbitantly high.

Figure 9:
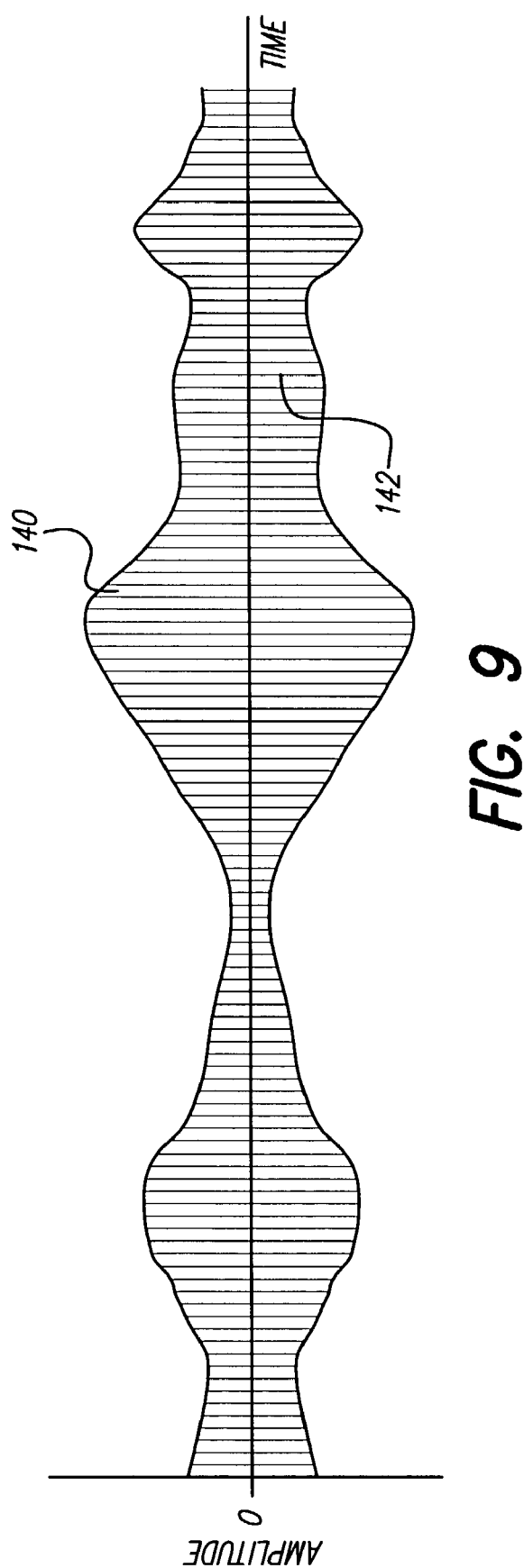
FIG. 9 depicts an auto-conditioning with high resolution (ACHR) pulse train of the type utilized by the present invention.

In contrast to the analog approach proposed by Rubinstein et al. (see FIGS. 8A and 8B), the present invention utilizes an auto-conditioning with high resolution (ACHR) neurostimulation approach. Such ACHR approach does not use an analog signal at all, thereby preserving significant power. The ACHR approach involves generating a high rate pulsatile signal, e.g., a biphasic pulse train having a rate greater than about 2000 Hz (i.e., having a period T less than about 500 µS), and having a selected pulse width (PW) within the range of from about 2–3 µS (microseconds) to about 75 µS. By way of example, the pulse width may be from between about 11 µS to about 21 µS for most patients. However, it is generally preferred to make the pulse width as narrow as the particular bionic ear implant will support. The frequency of stimulation, on the other hand, while it should be high, e.g., greater than about 2000 Hz, need not necessarily be much faster than whatever rate is determined as the desired high rate. (As the pulse width narrows, and the frequency or rate remains substantially the same, the duty cycle of the ACHR signal decreases, which helps reduce power consumption.) See FIG. 1 for a definition of the period, T, and the pulse width, PW. Such high rate pulsatile signal is amplitude modulated with the sound information, e.g., sound information sensed through the external microphone 18 and conditioned by the analog front end (AFE) circuitry (see FIG. 2B). Thus, when viewed on a large time scale, e.g., of several milliseconds (mS), the ACHR pulsitile signal provided by the bionic ear cochlear implant appears as shown in FIG. 9. In FIG. 9, the relatively slow-varying envelope 140 represents the variance in the sound information sensed through the external microphone (or other acoustic sensor); whereas the vertical lines 142 represent the individual biphasic pulses that are present in the ACHR signal. The spacing of the vertical lines 142 is not drawn to scale.

Figure 10:
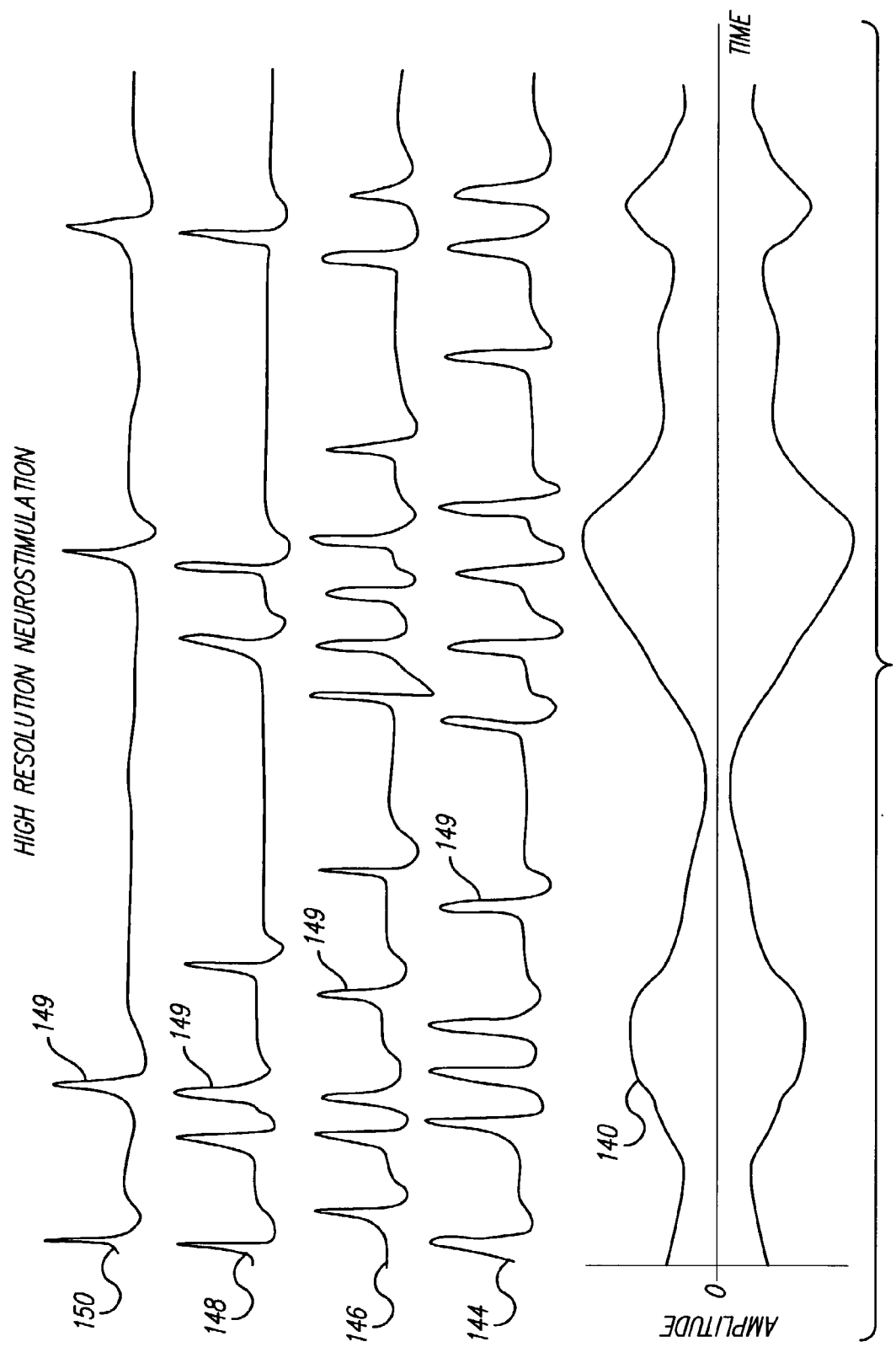
FIG. 10 conceptually illustrates how auto-conditioning with high resolution neurostimulation induces stochastic neural firing of all adjacent neurons.

FIG. 10 shows the effect achieved when the ACHR signal of FIG. 9 is applied through multiple electrode contacts to the auditory nerve fibers. The envelope 140 that modulates the amplitude of the ACHR signal is shown at the bottom of FIG. 10. The waveforms 144, 146, 148 and 150 represent neural firings that occur on various ones of the nerve fibers in the population of acoustic nerve fibers that are stimulated by the ACHR stimulation waveform, with each individual firing being represented by a respective spike 149 in the waveform.

Figure 11:
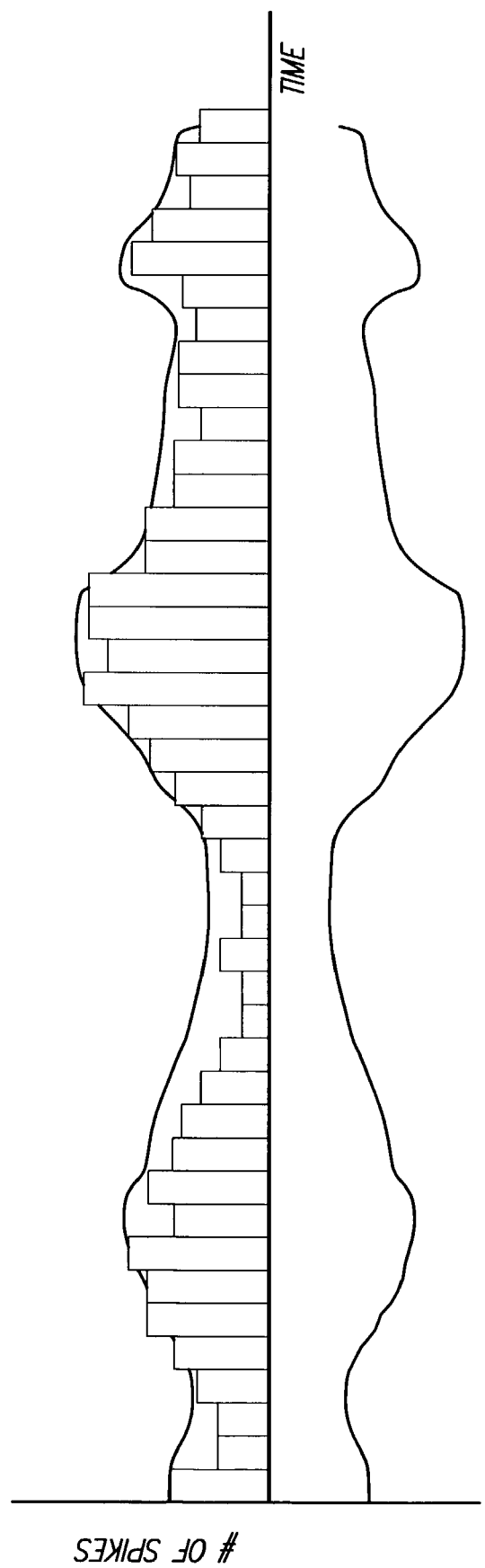
FIG. 11 illustrates a spike count histogram for the ACHR neurostimulation provided by the invention.

FIG. 11 shows a representative spike count histogram that results from application of the ACHR stimulation waveform to a given channel of a bionic ear implant. As is evident from FIG. 11, random or stochastic neural firing is achieved, thereby allowing thresholds, dynamic range and pyscophysical performance to be enhanced.

One of the key advantages made possible through use of the present invention is that T levels need not be measured for many, if not most, patients. Rather, the T level may be assumed to be 0 or some other value, e.g., 1/10 of the M value for a given channel.

To further explain why T levels may not be needed in all patients, consider that a threshold represents the intensity of signal X that meets an arbitrary detection criteria by system Y. The threshold (T) of X by Y is only valid for signal X. The system Y has inherent noise. If the system noise is altered, the T for X is likewise altered. In other words, a given T is specific for both the signal X as well as for the system noise of Y.

In traditional cochlear implant fittings, the value of T is determined by the activation of a single channel using a simple signal. The intensity of this signal that meets the detection criterion is called T. This T is then assumed to be appropriate for the system during "live speech" mode in which all channels are activated. However, the system noise of the neural detector Y is substantially different from single channel to live speech mode, resulting in a T mismatch. This means that all the effort undertaken to determine the T level may, in fact, be wasted effort for many patients because the T level thus determined doesn't fit the live speech mode.

Patent data indicate that thresholds set in single channel psychophysics, painstakingly measured, overestimate the actual threshold required when all channels are running during live speech. Such an overestimation appears to penalize patient performance, particularly performance in noise. It has been empirically determined that for many patients, because the T level is apparently very close to the noise level, the T level can simply be set to 0, or some other arbitrary level, thereby eliminating the need to go through the painstaking process of measuring T.

Patient data further indicate that when using high stimulation rates, the detectability of low level signals is enhanced such that certain patients actually gain performance benefits without the use of T levels during live speech mode. A similar effect appears to be present for simultaneous analog stimulation (SAS) in which T values are not used.

Since single channel measurements at high rates and at narrow pulse widths are made difficult by possible adaptation and shallow loudness growth, the relative shape of the upper level contour (most comfortable level M) may be determined at a wider pulse width. This upper level contour may then be linearly scaled to give the patient the appropriate volume.

In addition to setting T levels at zero or some other relatively low level, e.g., 1/10 of the measured M-levels, thereby significantly saving fitting time and complexity, the present invention further recognizes that T levels may be set using live speech. One method of setting T levels using live speech is as follows: Detectability is assessed by sweeping tones at the center frequencies (CF) of each channel's filter band while the patient is at a comfortable volume in live speech mode. If detectability meets the audiogram criteria without a T setting, then no T setting is used; otherwise, T is increased during live speech to give desired detectability on a channel-by-channel basis.

Another manner in which T levels may be set using live speech is as follows: The relative T and M contours are determined at a wider pulse width. M is globally adjusted in live speech to patient comfort. M is then set to be equal to T by setting the volume to zero on the sound processor. Live-speech is then pulsed on and off and the T contour is then globally shifted until a threshold criteria of detecting the global T pulse is determined.

Figure 12:
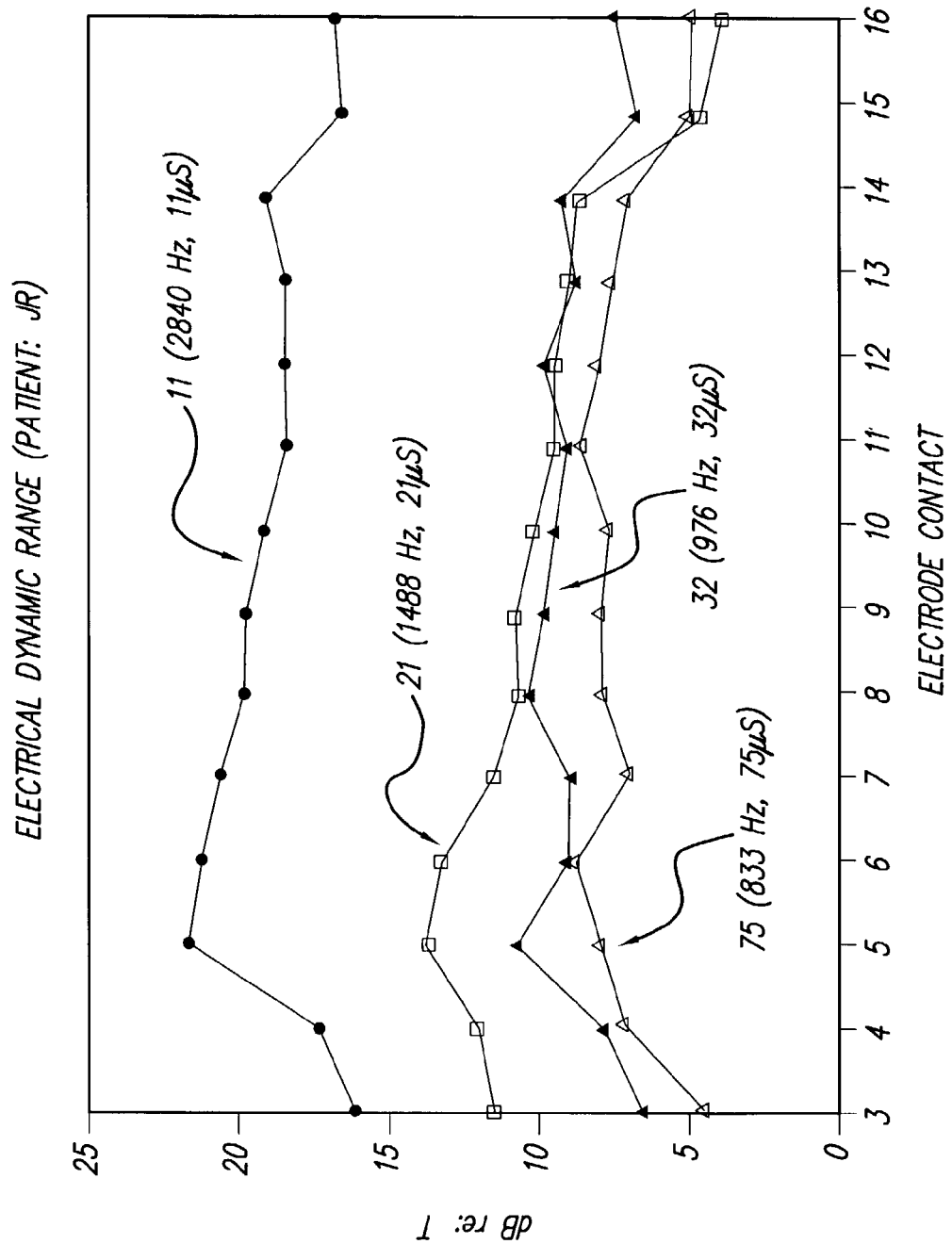
FIG. 12 is a graph showing the electrical dynamic range achieved using high resolution neurostimulation of differing parameters.

Using the techniques of the present invention, significant enhancements in patient performance have been observed. For example, FIG. 12 illustrates electrical dynamic range (vertical axis) as a function of electrode contact (horizontal axis) for various rates of an ACHR signal achieved by patient "JR" using the stimulation technique of the present invention. As seen in FIG. 12, dynamic range is expanded to approximately 20 dB (relative to the T level dynamic range) when a high rate stimulation signal (2840 Hz), having pulse widths of 11 μS, is employed. The dynamic range is on the order of 10 dB (re: T), when the stimulation rate is 1488 Hz and the pulse width is 21 μS. Other data shown in FIG. 12 are for a stimulation rate of 976 Hz and a pulse width of 32 μS; and a stimulation rate of 833 Hz and a pulse width of 75 μS.

Appendix A provides an overview of one type of fitting software that may be used with the invention, e.g., to set the T levels to some low value. By way of example, the T-levels may be set to a small fraction of the measured M-levels, e.g., 1/10 of the measured M levels. By not having to measure individual T levels on each channel, significant time is saved during the fitting process.

As described above, it is seen that a bionic ear implant allows populations of neuron fibers to be stimulated at a rate that is faster than an individual neuron fiber is able to follow. Advantageously, such fast stimulation results in a randomization of interspike intervals, or a randomization of when the individual neuron fibers fire. When the neuron is no longer phase-locked to the carrier pulse, its firing probability becomes a function of stimulus energy, and thus becomes more like "natural" hearing. Such randomization in a neural population better enables the population of neuron fibers to encode the fine details of sound. That is, the population of neuron fibers is able to encode what a single neuron fiber is not able to encode.

Further, as described above, it is seen that by restoring stochastic firing to the auditory nerve, thresholds, dynamic range and pyscophysical performance may be significantly enhanced.

While the invention herein disclosed has been described by means of specific embodiments and applications thereof, numerous modifications and variations could be made thereto by those skilled in the art without departing from the scope of the invention set forth in the claims.

What is claimed is:

1. A method of fitting a bionic ear implant having an electrode array with multiple electrode contacts through which electrical stimulation may be applied to the patient's cochlea; the method comprising:
    measuring M-levels associated with a stimulus applied to selected ones of the multiple electrode contacts, where an M-level comprises a comfortable stimulation intensity;
    globally determining a T-level for all of the electrode contacts, where a T-level comprises a minimally perceptable stimulation intensity; and
    using the M- and T-levels to help set the intensity of stimuli applied to the electrode contacts after fitting, wherein globally determining a T-level comprises setting the T-level to zero as the determined T-level.

2. A method of fitting a bionic ear implant having an electrode array with multiple electrode contacts through which electrical stimulation may be applied to the patient's cochlea; the method comprising:
    measuring M-levels associated with a stimulus applied to selected ones of the multiple electrode contacts, where an M-level comprises a comfortable stimulation intensity;
    globally determining a T-level for all of the electrode contacts, where a T-level comprises a minimally perceptable stimulation intensity; and
    using the M- and T-levels to help set the intensity of stimuli applied to the electrode contacts after fitting, wherein globally determining a T-level comprises setting the T-level to a value that is a prescribed fraction of the measured M-level.

3. A method of fitting a bionic ear implant having an electrode array with multiple electrode contacts through which electrical stimulation may be applied to the patient's cochlea; the method comprising:
    measuring M-levels associated with a stimulus applied to selected ones of the multiple electrode contacts, where an M-level comprises a comfortable stimulation intensity;
    globally determining a T-level for all of the electrode contacts, where a T-level comprises a minimally perceptable stimulation intensity; and using the M- and T-levels to help set the intensity of stimuli applied to the electrode contacts after fitting, wherein globally determining a T-level comprises setting the T-level to a value that is a prescribed fraction of the measured M-level; and wherein setting the T-level to a prescribed fraction of the measured M-level comprises setting the T-level to be 1/10 of the measured M-level.

4. A method of fitting a multichannel bionic ear implant, the bionic ear implant having multiple channels coupled to multiple electrode contacts of an electrode array, the bionic ear implant having means for applying electrical stimulation to the patient's cochlea through the electrode contacts of the electrode array; the method comprising:

measuring M-levels associated with a stimulus applied to selected ones of the multiple electrode contacts, where an M-level comprises a comfortable stimulation intensity;

determining a T-level for each channel using live speech, where a T-level comprises a minimally perceptable stimulation intensity; and using the M- and T-levels of each channel to help set the intensity of stimuli applied to the electrode contacts after fitting, wherein determining a T-level using live speech comprises:

sweeping tones at a center frequency of each channel while the bionic ear implant is set to a comfortable volume in live speech mode; and assessing whether the tones are detected in each channel without a T setting, and if so not using a T-setting on that channel, and if not increasing a T-setting on that channel during live speech to give desired detectability.

* * * * *